United States Patent [19]

Sunaga

[11] Patent Number: 4,501,477
[45] Date of Patent: Feb. 26, 1985

[54] LENS ADAPTER FOR ENDOSCOPES

[75] Inventor: Yasumasa Sunaga, Iwatsuki, Japan

[73] Assignee: Fuji Photo Optical Co., Ltd., Ohmiya, Japan

[21] Appl. No.: 487,149

[22] Filed: Apr. 21, 1983

Related U.S. Application Data

[63] Continuation of Ser. No. 217,470, Dec. 17, 1980, abandoned.

[30] Foreign Application Priority Data

Dec. 26, 1979 [JP] Japan ............................ 54-169586

[51] Int. Cl.³ .............................................. G02B 7/04
[52] U.S. Cl. ................................. 350/560; 350/96.26; 350/572; 350/410; 350/422
[58] Field of Search ............... 350/560, 572, 573, 410, 350/422, 96.25, 96.26

[56] References Cited

U.S. PATENT DOCUMENTS

| 1,553,211 | 9/1925 | Barr et al. | 350/422 |
| 2,165,341 | 7/1939 | Capstaff et al. | 350/427 X |
| 3,638,996 | 2/1972 | Klein | 350/410 |
| 4,285,578 | 8/1981 | Yamashita et al. | 350/410 |

Primary Examiner—Davis L. Willis
Assistant Examiner—Matthew W. Koren

[57] ABSTRACT

A variable focal length lens adapter is attached to an endoscope at its eyepiece. The lens adapter includes a lens system constituting a variable focal length lens system in combination with the eyepiece. The lens system of the lens adapter is composed of a negative lens group located next to the eyepiece, a positive lens group located next to the negative lens group and a second negative lens group located next to the positive lens group on the side opposite to the first negative lens group. The first negative lens group and the positive lens group are axially movable to vary the focal length of the total lens system of the adapter. The last negative lens is used as a diopter adjusting lens.

3 Claims, 2 Drawing Figures

4,501,477

LENS ADAPTER FOR ENDOSCOPES

This is a continuation of application Ser. No. 217,470, filed Dec. 17, 1980, abandoned.

BACKGROUND OF THE INVENTION

1. Field of the Invention

This invention relates to an adapter to be mounted on the eyepiece of an endoscope, and more particularly to an adapter having the function of varying the magnification of the eyepiece.

2. Description of the Prior Art

Concerning the endoscope, a device for viewing the interior of a human body, it is highly desirable that the angle of view of the endoscope be enlarged. By enlarging the angle of view of the endoscope, the thickness of the flexible tube can be reduced. A thinner tube is highly desirable since it decreases the possibility of pain when inserted into the body.

On the other hand, by enlarging the angle of view or reducing the thickness of the tube, the size of the image observed through the eyepiece is reduced and the device's diagnostic efficiency and accuracy are lowered. Further, the eyes are likely to be easily tired viewing this reduced image, the effectiveness of forceps is lessened and cannulation into the duodeunum becomes difficult. Concerning the use of forceps, it is very difficult for doctors accustomed to handle forceps with a conventional angle of view or magnification to operate with a wide angle view.

Thus, there is now a demand for an endoscope having a wide angle view which is capable of reducing the angle of view when desired, such as times when forceps are being used.

SUMMARY OF THE INVENTION

The primary object of the present invention is to provide an adapter to be mounted on the eyepiece of an endoscope for varying the effective magnification or field of view of the endoscope.

A more specific object of the present invention is to provide a magnification variable lens adapter for an endoscope which is capable of varying the magnification of the eyepiece lens from the conventional 18 to 22 times to as much as 40 times.

The adapter, in accordance with the present invention, is characterized by a variable lens system composed of the eyepiece of the endoscope and the lens system contained in the adapter. In further detail, the lens group of the variable lens system comprises a negative lens group, a positive lens group and a negative lens group arranged in this order in which the space between the central positive lens group and the negarive lens group located on the eyepiece side is variable for varying the magnification.

DESCRIPTION OF PREFERRED EMBODIMENT

Figure 1:
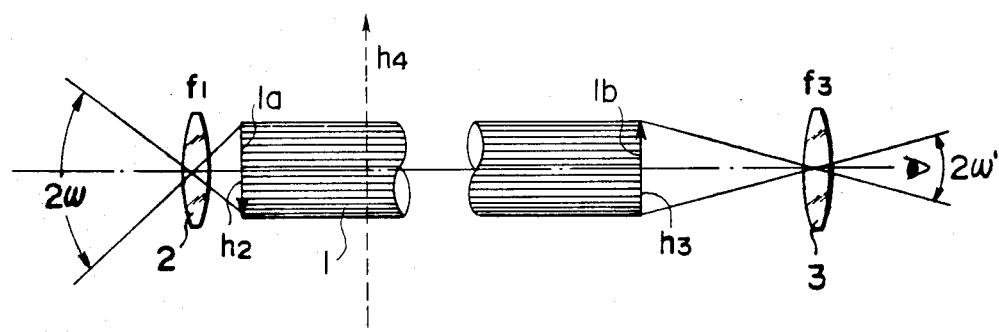
FIG. 1 is a side view showing the whole optical system of an endoscope to which the lens adapter of this invention is to be mounted.

Now the invention will be described in detail referring to the drawings. Before describing the structure of the adapter of this invention, there will be made description of the whole optical system of an endoscope referring to FIG. 1.

FIG. 1 shows the whole optical system of an endoscope to which the adapter of the present invention is to be mounted. The endoscope is mainly composed of an image-guiding flexible tube 1 having the entrance face 1$a$ for receiving light from the interior to be observed or photographed and an exit face 1$b$ from which the image of the interior can be viewed. At the entrance face 1$a$ a wide angle objective 2 is provided for focusing an image of the object or the interior to be observed or photographed on the entrance 1$a$ with a wide angle of view. At the exit face 1$b$ an eyepiece lens system 3 is provided for viewing the image. In more detail, on the entrance face 1$a$ of the image guiding flexible tube or optical fiber bundle 1 is focused an image $h_2$ by the objective 2, and on the exit face 1$b$ of the image guiding flexible tube 1 appears an image $h_3$. By an eyepiece 3 having a focal length of $f_3$ a virtual image $h_4$ of the image $h_3$ is viewed in enlarged scale. In accordance with this invention, a variable focal length eyepiece adapter 4, 5, 6 (See FIG. 2) is mounted on the eyepiece 3 to enable viewing the image $h_3$ at a desired magnification.

In an endoscope employing the conventional optical system, the angle of view $2w$ of the objective 2 is about 60° to 70°, and the magnification of the eyepiece is normally 18 to 22 times and the effective angle of view $2w'$ is about 8° to 12°. Under the circumstances, when the angle of view of the objective 2 is enlarged to 100° or more ($2w \geq 100°$), the angle of view is enlarged to about 1.5 times to 2 times as large as the conventional one. However, the size of the image $h_2$ focused on the entrance face 1$a$ of the image guiding tube cannot be made so large due to restriction as to the outer diameter of the endoscope. Therefore, the image magnification of the image $h_2$ cannot be enlarged over 1.2 times as large as the conventional one. Consequently, with said effective angle of view of the eyepiece, the size of the image appearing on the exit face 1$b$ of the image guiding tube 1 becomes small and is viewed in reduced scale. This is disadvantageous in that the image is hard to see for the observer who is accustomed to see the conventional size image. In order to solve this problem, it is possible to increase the magnification of the eyepiece which results in enlargement of the size of the virtual image $h_4$. However, if the magnification of the eyepiece is enlarged, the appearance of the exit face 1$b$ of the optical fiber bundle 1 is also enlarged and the image quality of the observed image is deteriorated. Thus, it is undesirable to enlarge the image magnification over a certain value. On the other hand, when the magnification of the eyepiece 3 is too much increased in this invention, the adapter lens system becomes too large and heavy. Therefore, from this viewpoint also, it is undesirable to increase the magnification over a certain value. In view of these considerations, the magnification of the eyepiece or the focal length varying ratio is desired to be made about twice.

Further, it will be noted that the variable focal length eyepiece adapter lens system 4, 5 is advantageous in comparison with an eyepiece lens system having a discontinuously changeable focal length in that the size of the image can easily and instantly be varied to any desired value.

Further, it will be understood that there may be used a mask in the optical path of the endoscope, for instance between the exit face 1$b$ and the eyepiece 3, when it is not necessary to see the whole the field of view of the image or it is desired to cut a part of the field of view.

Figure 2:
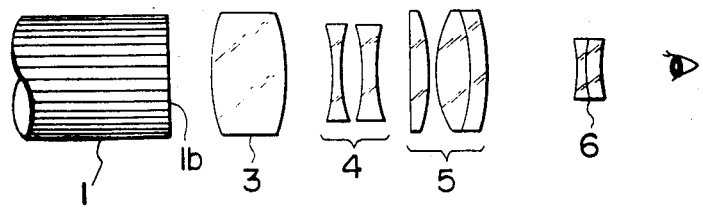
FIG. 2 is a side view showing an embodiment of the lens adapter in accordance with the present invention.

Now referring to FIG. 2, the lens adapter 4, 5, 6 in accordance with the present invention is composed of a negative lens group 4 located adjacent the eyepiece 3, a positive lens group 5 located next to the negative lens group 4 and a negative lens group 6 located adjacent the positive lens group 5. In other words, the positive lens group 5 is sandwiched between a pair of negative lens group 4 and 6. The parallel light rays emanating from the end face 2 of the fiber bundle 1 is diverged by the first negative lens group 4, converged by the positive lens group 5 and then again diverged into parallel rays by the second negative lens group 6. Thus, the parallel light rays enter the eyes 7 of an observer.

In the adapter lens system, the first negative lens group 4 and the positive lens group 5 are axially movable to vary the magnification of the total lens system, including the eyepiece 3 and the adapter lens system 4, 5 and 6. In other words, the total effective focal length of the lens system comprising the eyepiece 3 and the adapter lens system 4, 5 and 6 is made variable by moving the first negative lens group 4 and the positive lens group 5.

The reasons for arranging the lens system as mentioned above are:

(1) the parallel light rays from the eyepiece 3 are made parallel through the negative lens group 6, (2) an eyepoint distance from the second negative lens group 6 to the eyes 7 is easily obtained, and (3) the second negative lens group 6, which is fixed, can be used as a diopter adjuster.

The adapter can be easily attached to any kind of endoscope without modifying the structure of the conventional endoscope. Further, it is also possible to attach a camera or any other accessory to the adapter by making the external structure of the adapter the same as that of the eyepiece portion of the conventional endoscope.

Since the adapter, in accordance with the present invention, is capable of varying the magnification of the image viewed through the eyepiece of an endoscope to which it is attached, the practical advantages in diagnoses and treatments of ulcer and cancer are markedly great.

As will readily be understood, the adapter lens system consisting of the three lens groups 4, 5 and 6 is held in a lens barrel or an adapter lens body (not shown) and is demountably attached to the eyepiece portion of the endoscope. The means for demountably attaching the adapter lens body to the eyepiece portion of the endoscope may be of any type. For example, any means conventionally used for demountably mounting a camera to the eyepiece portion of the endoscope can be employed. The means for attaching the adapter body to the endoscope may be provided on the endoscope side. In that case, the adapter body may only be made into a configuration that can be demountably attached to the eyepiece portion of the endoscope by use of said attaching means provided on the endoscope side.

I claim:

1. In combination: an endoscope having an optical fiber bundle with an entrance face at one end thereof and an exit face at the other end thereof, an eyepiece having a fixed focal length located adjacent said exit face for viewing an image appearing on said exit face, a wide angle objective lens adjacent said entrance face for focussing an image to be observed on said entrance face, and an adapter for varying the magnification of the image viewed through said eyepiece, said adapter comprising an adapter body, means for demountably attaching said adapter body to said eyepiece, said adapter also comprising an axially movable negative lens group, an axially movable positive lens group, and a fixed negative lens group, said groups being arranged in the above order away from said eyepiece and said exit face towards a viewer.

2. The combination of claim 1, wherein said movable negative lens group and said positive lens group are axially movable for varying the focal length of the combination of said eyepiece and the lens groups in said adapter body.

3. The combination according to claim 1, wherein said fixed negative lens group is a diopter adjusting lens group.

* * * * *